United States Patent [19]

Sorensen

[11] Patent Number: 4,924,873
[45] Date of Patent: May 15, 1990

[54] PNEUMATIC CONTROL SYSTEM FOR NEONATAL BLOOD PRESSURE MONITORING

[75] Inventor: Jay R. Sorensen, Washington, Oreg.

[73] Assignee: SpaceLabs, Inc., Bothell, Wash.

[21] Appl. No.: 172,287

[22] Filed: Mar. 23, 1988

[51] Int. Cl.⁵ .................................................. A61B 5/02
[52] U.S. Cl. ..................................... 128/677; 128/685
[58] Field of Search ................. 128/672, 677, 680–686

[56] References Cited

U.S. PATENT DOCUMENTS

| | | | |
|---|---|---|---|
| 2,811,964 | 11/1957 | Boucke | 128/685 |
| 3,157,177 | 11/1964 | Smith | |
| 3,978,848 | 9/1976 | Yen et al. | 128/681 |
| 4,116,230 | 9/1978 | Gorelick | 128/682 |
| 4,210,154 | 7/1980 | Klein | 128/686 X |
| 4,378,807 | 4/1983 | Peterson et al. | 128/680 X |
| 4,627,440 | 12/1986 | Ramsey, III et al. | 128/682 |
| 4,671,290 | 6/1987 | Miller et al. | |
| 4,774,960 | 10/1988 | Arnold et al. | 128/681 |

FOREIGN PATENT DOCUMENTS

| | | | |
|---|---|---|---|
| 208520 | 4/1986 | European Pat. Off. | |
| 2948067 | 6/1981 | Fed. Rep. of Germany | 128/685 |
| 2165052 | 4/1986 | United Kingdom | |

Primary Examiner—Angela D. Sykes
Attorney, Agent, or Firm—Seed and Berry

[57] ABSTRACT

A control system for a blood pressure monitor having a blood pressure cuff, an air pump for inflating the cuff, a pressure transducer measuring the air pressure in the cuff, and a bleed valve for selectively venting the blood pressure cuff to reduce the cuff pressure. The air pump leaks air when it is de-energized, thereby inadvertently leaking air from the blood pressure cuff when the air pressure in the cuff is to be maintained constant as an attempt is made to detect blood flow beneath the cuff. A two-way valve is placed in series with the air pump to isolate the air pump from the cuff when the pressure in the cuff is to be maintained constant. The two-way valve allows air to leak from the blood pressure cuff through the air pump when the cuff is to be vented. The two-way valve and the bleed valve thus provide redundant venting of the blood pressure cuff. The bleed valve and the two-way valve shift to their cuff-venting positions when they are de-energized so that the cuff is assured of venting in the event of a power loss in said monitor.

9 Claims, 3 Drawing Sheets

PNEUMATIC CONTROL SYSTEM FOR NEONATAL BLOOD PRESSURE MONITORING

DESCRIPTION

1. Field of the Invention

This invention relates to blood pressure monitoring systems, and more particularly, to a system for pumping air into a blood pressure monitoring cuff, preventing inadvertent leakage of air from the cuff during a blood pressure measurement, and providing two independent leakage paths from the cuff after the measurement.

2. Background Art

Blood pressure monitors are commonly used to take blood pressure measurements without nursing assistance. Typical blood pressure monitors include an air pump that supplies pressurized air to a conventional blood pressure cuff and a pressure transducer that measures the pressure of air in the cuff.

In making a blood pressure measurement, the air pump is energized for a predetermined period to inflate the cuff. After the cuff has been inflated, an electronic or acoustic audio pickup is used to determine if blood is flowing in an artery beneath the cuff during both the systolic and diastolic portions of the heart cycle. The air pressure in the cuff is measured, at all times, by the pressure transducer. Blood flow is normally not detected as soon as the cuff is fully inflated since the cuff pressure is then at its maximum value. If no blood flow is detected, the air is rapidly bled from the cuff until the pressure has been reduced an incremental value. The cuff pressure is once again held at that value while an attempt is made to detect blood flow in the artery during the systolic and diastolic portions of the heart cycle. This cycle of incremental pressure reduction, pressure hold, and blood flow detection is repeated until blood flow is detected during both the systolic and diastolic portions of the heart cycle. The cuff pressure at which blood starts to flow during systole is recorded as the systolic blood pressure, while the cuff pressure at which blood starts to flow during diastole is recorded as the diastolic blood pressure.

In a manual blood pressure monitor, the operation of the air pump and valve may be manually controlled. However, most of the above-described blood pressure monitors are automatic and they take blood pressure measurements on a periodic basis. These automatic blood pressure monitors utilize conventional electronic timing and control circuits to periodically trigger the start of a measurement and to then control the energization of the air pump and valve, record the resulting air pressures in the cuff, and detect the presence of blood flow in an artery beneath the cuff.

The conventional air pumps used in manual and automatic blood pressure monitors have a tendency to leak air during blood pressure measurements. This inadvertent leakage can adversely affect the accuracy of blood pressure measurements because the air pressure in the cuff will be changing while a measurement is being taken. Furthermore, the rate of leakage is not uniform even for the same model of pump, so the leakage cannot be compensated for by the monitor. Despite this inadvertent leakage, conventional air pumps are adequate for use in blood pressure monitors for adults because the blood pressure cuffs used by adults have relatively large air volumes. As a result, the leakage has a relatively small effect on the pressure in the cuff. However, blood pressure cuffs used for neonatals have air volumes that are substantially smaller than the air volumes of adult blood pressure cuffs. As a result of this relatively small volume, the inadvertent leakage through air pumps can have a drastic effect on the pressure in neonatal blood pressure cuffs. This leakage can, therefore, adversely affect the accuracy of blood pressure monitors used for neonatals.

The above-described problems with conventional neonatal blood pressure monitors have been known for some time. However, prior attempts to solve these problems have not been successful. One conventional approach is to place a one-way check valve in series with the air pump to theoretically block the reverse flow of air through the pump. However, conventional check valves have been incapable of adequately blocking the reverse flow of air at the relatively low air pressures in neonatal blood pressure cuffs. As a result, inadvertent leakage continues to exist, thereby degrading the accuracy of neonatal blood pressure measurement.

Another problem with conventional blood pressure monitors stems from their inability to bleed air from the blood pressure cuff each time the pressure is to be incrementally reduced. As mentioned above, an air valve is actuated to bleed the air from the cuff to reduce the cuff pressure by an incremental value until blood flow is detected during both systole and diastole. If the valve fails, the intended path of leakage does not exist and the blood pressure cuff remains inflated for an exceptionally long period. Prolonged inflation of blood pressure cuffs is undesirable because it can cause discomfort to the patient. This problem is particularly acute where attempts have been made to prevent the reverse flow of air through the air pump, thereby further prolonging the inflation of the cuff.

DISCLOSURE OF THE INVENTION

It is an object of the invention to provide a blood pressure monitoring system which prevents the inadvertent leakage of air from a blood pressure cuff.

It is another object of the invention to provide a blood pressure monitoring system that will not unduly prolong the inflation of a blood pressure cuff in the event of a failure of the air bleed valve for the system.

It is still another object of the invention to prevent prolonged inflation of a blood pressure cuff in a manner that does not exacerbate inadvertent air leakage problems in blood pressure monitors.

It is a further object of the invention to provide an improved blood pressure monitor of the character described utilizing conventional, commonly available components.

These and other objects of the invention are provided by a pneumatic control system for blood pressure monitors having an inflatable blood pressure cuff. The control system includes an air pump generating pressurized air in its energized condition and allowing air to leak through the pump in the reverse direction when the pump is de-energized. A first valve is connected between the air pump and blood pressure cuff. The first valve has a first position allowing airflow between the air pump and blood pressure cuff and a second position isolating the air pump from the blood pressure cuff. A second valve is connected between the blood pressure cuff and the atmosphere. The second valve has a first position allowing airflow between the blood pressure cuff and one air vent and a second position isolating the blood pressure cuff from the atmosphere.

A control circuit selects between inflate, hold, and deflate conditions. In the inflate condition, the control circuit energizes the air pump, switches the first valve to its first position, and switches the second valve to its second position. In the hold condition, the control circuit de-energizes the air pump and switches the first and second valves to their second positions. In the deflate condition, the control circuit de-energizes the air pump and switches the first and second valves to their first positions. As a result, the air pump is isolated from the air cuff in the hold condition and the air cuff is vented through both valves in the deflate condition. The first and second valves are preferably in their first positions when they are de-energized and switch to their second positions when they are energized so that both valves vent the blood pressure cuff when they are de-energized. As a result, the cuff is vented in the event of a power loss in the control system.

BEST MODE FOR CARRYING OUT THE INVENTION

Figure 1:
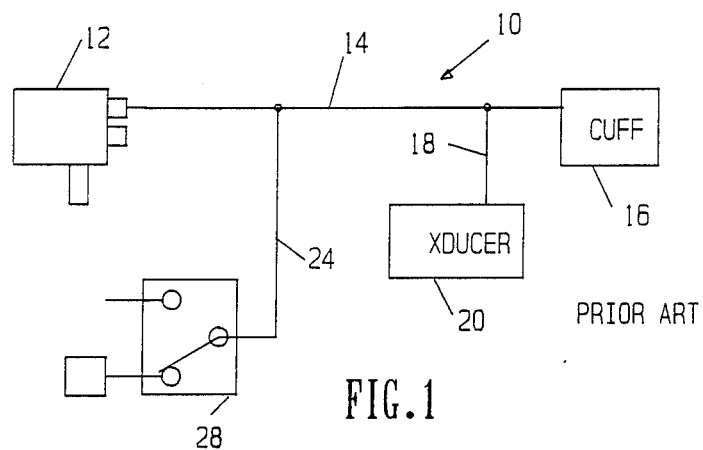
FIG. 1 is a schematic of a commonly used prior art blood pressure monitor.

A conventional blood pressure monitor 10, as illustrated in FIG. 1, includes a conventional air pump 12 connected through a pneumatic line 14 to a conventional blood pressure cuff 16. Another pneumatic line 18 extends from line 14 to a conventional pressure transducer 20. The transducer thus measures the pressure of the air in the blood pressure cuff 16 after it is inflated by the air pump 12. A third pneumatic line 24 extends from line 14 to a two-way valve 28. In its first position, the valve 28 vents line 24 to atmosphere. In its second position, the valve 24 effectively prevents air from leaking from line 24. Conventional, well-known electronic circuits control the air pump 12 and valve 28 and interface with the pressure transducer 20. These circuits need not be understood to understand the subject matter of the invention, and their description has, therefore, been omitted in the interests of brevity.

As mentioned above, when a blood pressure measurement is to be taken, the air pump 12 is energized to inflate the cuff until the pressure transducer 20 registers a predetermined pressure. An attempt is then made to detect blood flow in an artery beneath the cuff during both systole and diastole using an electronic or acoustic audio pickup (not shown). The air pressure in the cuff is measured, at all times, by the pressure transducer 20. Assuming that blood flow in not initially detected, the valve 28 is actuated from its second position to its first position, thereby rapidly bleeding air from the cuff 16 until the pressure transducer 20 measures that the cuff pressure has been reduced an incremental value. The valve 28 is then shifted back to its second position to once again hold the air pressure in the cuff 16 constant while an attempt is made to detect blood flow. This cycle of incremental pressure reduction, pressure hold, and blood flow detection is repeated until blood flow is detected during both systole and diastole. The cuff pressure at which blood starts to flow during systole is recorded as the systolic blood pressure, while the cuff pressure at which blood starts to flow during diastole is recorded at the diastolic blood pressure.

The prior art blood pressure monitor illustrated in FIG. 1 exemplifies both of the problems solved by the inventive pneumatic control system. When the monitor 10 is attempting to detect blood flow, the air pressure in the cuff 16 should be constant in order to obtain an accurate measurement. However, even though the valve 28 is in its second position, air inadvertently bleeds from the cuff 16 through the air pump 12.

The second problem with conventional blood pressure monitors' failure to bleed air from the cuff 16 when desired is also present in the embodiment of FIG. 1. If the valve 28 fails in its second position and does not bleed air from the cuff 16, the inflation of the cuff 16 will be greatly prolonged, thereby causing undue discomfort to the patient whose blood pressure is being monitored.

Figure 2:
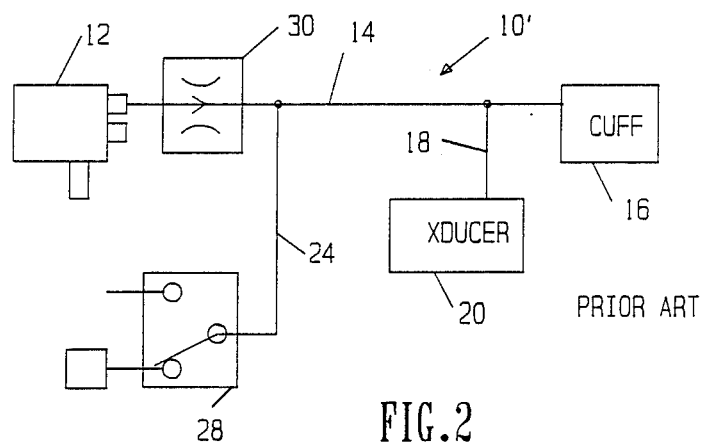
FIG. 2 is a schematic of a prior art modification of the blood pressure monitor of FIG. 1 that attempts to avoid the problem of inadvertent cuff leakage.

One approach to solving the problem of inadvertent air leakage from the cuff 16 is illustrated in FIG. 2. Most of the components used in the monitor 10' of FIG. 2 are common to the components used in the monitor 10 of FIG. 1, and they operate in the same manner in both monitors. Accordingly, these common components have been given the same reference numerals in FIG. 2, and in the interest of brevity, an explanation of their operation will not be repeated. The monitor of FIG. 2 adds a conventional one-way check valve 30 in series with the air pump 12 in an attempt to prevent the reverse flow of air through the air pump 12. However, conventional one-way check valves are not effective in preventing reverse flow at the relatively low pressures found in blood pressure cuffs. Furthermore, placing the one-way check valve 30 in series with the air pump 12 has no effect on the inability of the monitor 10' to bleed air from the cuff 16 when desired in the event of a failure of the valve 28.

A blood pressure monitor 40 that solves both of the problems inherent in conventional monitors is illustrated in FIGS. 3-6. The monitor 40 utilizes some of the same components operating in the same manner as in the monitors 10, 10' of FIGS. 1 and 2, respectively. Accordingly, these components have been given the same reference numerals in all cases. These common components include the air pump 12, blood pressure cuff 16, pressure transducer 20, and two-way valve 28. The inventive blood pressure monitor 40 further includes a second two-way valve 42 connecting the air pump 12 to the blood pressure cuff 16 in its first position and blocking all airflow to the air pump 12 in its second position.

Figure 3:
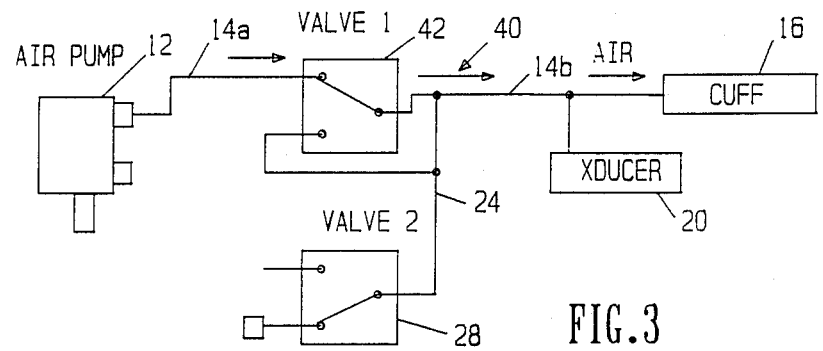
FIG. 3 is a schematic of the inventive blood pressure monitor shown during its inflation cycle.

The blood pressure monitor 40 is shown in FIG. 3 in the "inflate" portion of its operating cycle. In this operating phase, the air pump 12 is energized, the valve 42 is unenergized to connect the air pump 12 to the blood pressure cuff 16, and the valve 28 is energized to prevent air from being bled from the cuff 16. As the air pump 12 continues to inflate the cuff 16, the air pressure in the cuff is measured by the pressure transducer.

Figure 4:
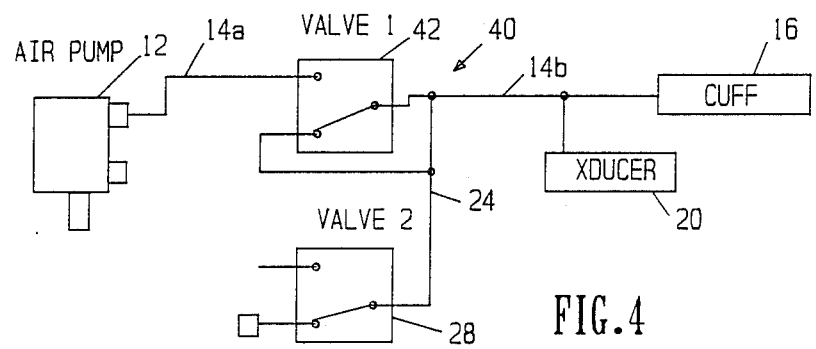
FIG. 4 is a schematic of the inventive blood pressure monitor shown during its measurement cycle.

When the air pressure reaches a predetermined value, the monitor 40 is switched to the "hold" portion of its operating cycle, as shown in FIG. 4. In the "hold" condition, the air pump 12 is de-energized, the valve 42 is energized to its second position to isolate the air pump 12 from the remainder of the system, and the valve 28 remains energized in its second position to prevent air from being bled from the cuff 16. The air pressure in the cuff 16 therefore remains constant as an attempt is made to detect blood flow since there in no leakage path from the cuff 16.

As mentioned above, blood flow does not normally occur at the initial fully inflated pressure of the cuff 16. Air is then bled from the cuff 16 until the pressure, as measured by the transducer 20, has fallen a predetermined increment. This pressure reduction is accomplished in the "deflate" portion of the operating cycle illustrated in FIG. 5. In this condition, the air pump 12 remains de-energized and the valve 42 continues to isolate the air pump 12 from the remainder of the system to prevent the reverse flow of air through the pump 12. However, the valve 28 is now de-energized to its first position to vent the blood pressure cuff 16 to atmosphere. When the pressure transducer detects that the air pressure in the cuff 16 has fallen a predetermined value, the monitor shifts back to the "hold" condition by energizing the valve 28 to its second position, in which airflow through the valve 28 is prevented. The monitor 40 continues to shift back and forth between the "hold" and "deflate" conditions and to detect any blood flow during each "hold" condition until blood flow has been detected during both systole and diastole. The monitor 40 then shifts to the "deflate" condition to bleed all of the air from the cuff 16 until the next measurement is to be taken.

It is important to note that the monitor not only prevents any leakage from the cuff 16 during the measurements, but it also ensures that the cuff 16 is vented after the measurements have been taken. Either of the valves 42 or 28 is capable of venting the cuff 16. The valve 28 vents the cuff 16 relatively quickly, but the valve 42 will also vent the cuff 16 through the air pump 12 with sufficient rapidity to prevent patient discomfort. Moreover, both of the valves 42, 28 are shifted to their respective venting position when they are de-energized. As a result, the cuff 16 is assured of being vented if either of the valves 42 or 28 is jammed in its energized position or if all power is lost to both valves 42, 28.

Figure 6:
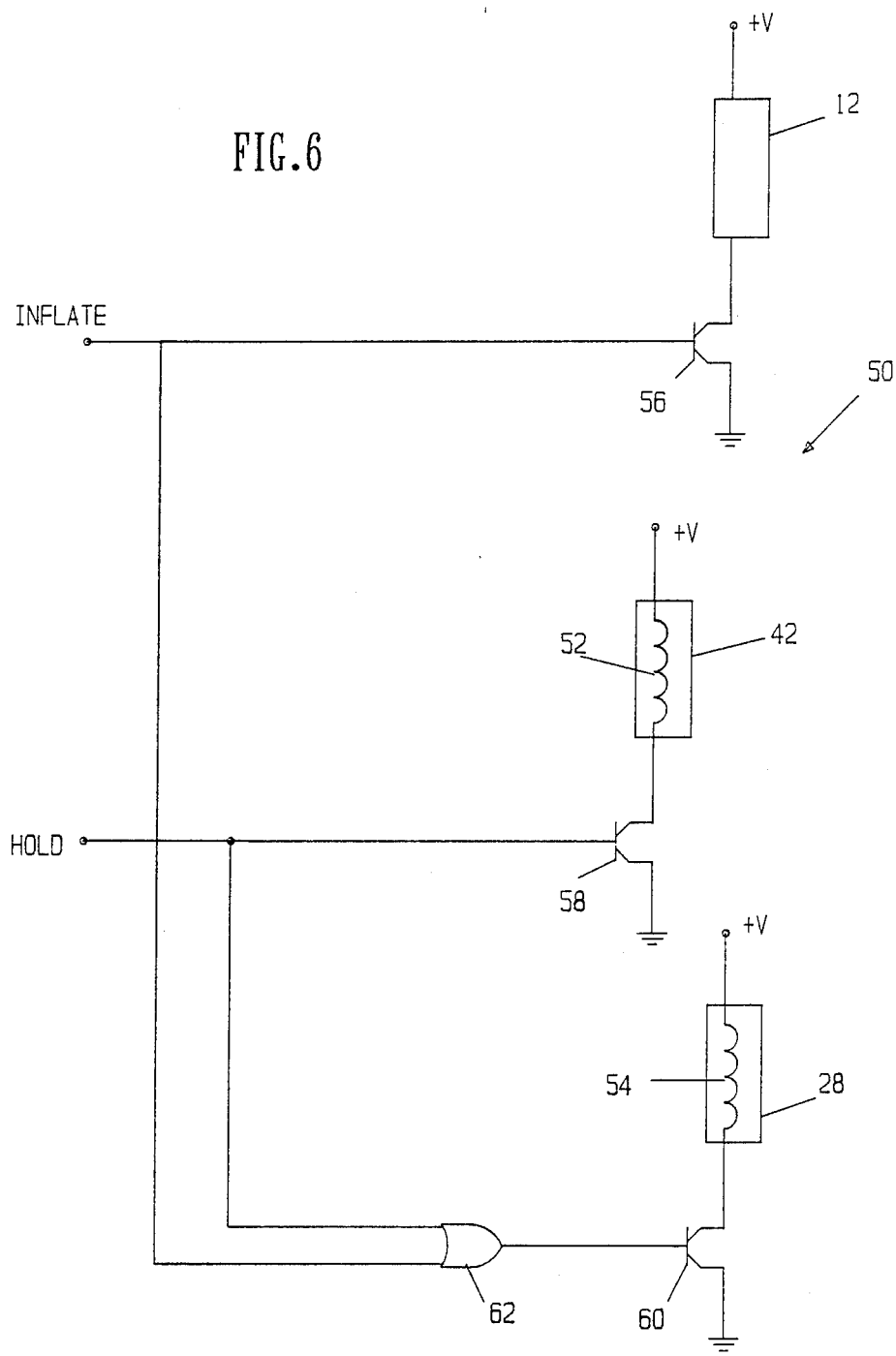
FIG. 6 is a schematic of a circuit for controlling the operation of the inventive blood pressure monitor during its inflation, measurement and deflation cycles.

Although the air pump 12 and valves 42, 28 may be controlled by circuitry that is similar to the circuitry used to control the operation of conventional monitors, one embodiment of a control circuit 50 is illustrated in FIG. 6. The circuit is operated by binary "inflate" and "hold" signals which may have a logic level of either "1" or "0." The absence of a high "inflate" or "hold" signal automatically signals the "deflate" condition. The "inflate" and "hold" signals may be generated either manually by respective switches or by conventional automatic timing and control circuits.

The pump 12, and actuating coils 52, 54 in the valves 42, 28, respectively, are each connected between a supply voltage and a respective field effect transistor (FET) switch 56, 58, 60. The drain of each FET 56, 58, 60 is connected to ground so that current flows through the FET when a logic "1" voltage level is applied to its respective gate. When the "inflate" input is "1," the FET 56 is turned on, thereby causing current to flow through and energize the air pump 12. The "1" logic level is also applied to the FET 60 through an OR gate 62 to pull current through the actuating coil 54 for the valve 28, thereby shifting the valve 28 to its second position, as illustrated in FIG. 3. The FET 58 remains turned off, so the valve 42 remains de-energized.

Figure 5:
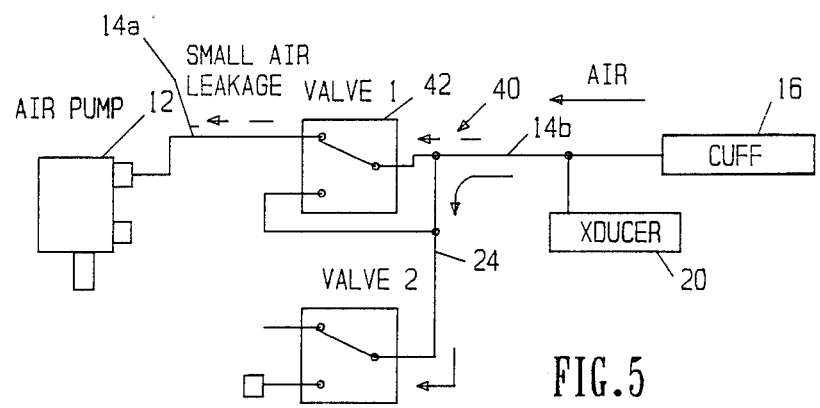
FIG. 5 is a schematic of the inventive blood pressure monitor shown during its deflation cycle.

When the "hold" condition is to be selected, the "hold" input rises to a logic "1," thereby turning on FETs 58 and 60. Current then flows through the actuating coils 52, 54 of the valves 42, 28, respectively, thereby energizing the valves 42, 28, as illustrated in FIG. 5.

When the "inflate" and "hold" signals are both at logic "0," none of the FETs 56, 58, 60 are turned on, so the air pump 12 and valves 42, 28 are all de-energized, as illustrated in FIG. 6.

While a specific embodiment of the inventive monitor is described, it will be understood that other components may be substituted without departing from the scope of the invention. For example, although the valves 28, 42 are described as being two-way valves, it will be understood that one-way valves can be used as long as the one-way valves isolate two pneumatic ports from each other when the valve is energized and connect the ports to each other when the valve is de-energized. Also, if leakage through the air pump 12 is not sufficient to vent the cuff 12 through the valve 42 and if the valve 28 sticks in its second position, a leakage path 46 may be installed at the air pump 12. The leakage path has no effect on the monitor 40 in the "hold" condition since the valve 42 isolates the air pump 12 from the remainder of the system. When the monitor 40 is in the "inflate" condition, the leakage path causes a slight but inconsequential decrease in the effective capacity of the pump 12. Finally, in the "deflate" condition, the leakage path causes faster venting of the cuff 12. However, since the rate of cuff deflation is irrelevant, the leakage path has no effect on the monitor in the "deflate" condition.

The inventive blood pressure monitor 40 avoids both of the problems inherent in conventional monitors, particularly when those monitors are used for neonatal applications. The monitor 40 thus not only prevents the inadvertent flow of air from the cuff 12, but it also ensures that air will be vented from the cuff when desired.

I claim:

1. A pneumatic control system for blood pressure monitors having an inflatable blood pressure cuff, said control system comprising:

an air pump generating pressurized air in its energized condition and allowing air to leak through said pump in a reverse direction when said pump is de-energized;

a first valve connected between said air pump and said blood pressure cuff, said first valve having a first position allowing airflow between said air pump and blood pressure cuff, and a second position isolating said air pump from said blood pressure cuff;

a pressure transducer measuring the air pressure in said blood pressure cuff;

a second valve connected between said blood pressure cuff and an atmospheric air vent, said second valve having a first position allowing airflow between said blood pressure cuff and said air vent, and a second position isolating said blood pressure cuff from said air vent; and control means selectable between inflate, hold and deflate conditions, said control means energizing said air pump, switching said second valve to its second position in said inflate condition, said control means de-energizing said air pump and switching said first and second valves to their second positions in said hold condition, and said control means de-energizing said air pump and switching said first and second valves to their first positions in said deflate condition, said air pump being isolated from said blood pressure cuff in said hold condition and said blood pressure cuff being vented through both of said valves in said deflate condition.

2. The control system of claim 1 wherein said first and second valves are in their first positions when they are de-energized and switch to their second positions when they are energized, whereby both of said valves vent said blood pressure cuff when they are de-energized so that said cuff is vented in the event of a power loss in said control system.

3. The control system of claim 1, further including a restricted flow leakage vent at said air pump to increase the reverse flow of air through said first valve in said deflate condition.

4. In a blood pressure monitor having an air pump that pumps air when energized and leaks air in a reverse direction when de-energized, a blood pressure cuff connected to said air pump through a conduit, a pressure transducer for measuring the pressure of the air in said cuff, a selectively actuated bleed valve for allowing air to vent from said cuff, and an audio pickup to detect blood flow in an artery beneath said blood pressure cuff when said cuff is worn by a patient, the improvement comprising a second valve connected in said conduit, said second valve allowing airflow between said pump and said cuff in one position and isolating said pump from said cuff in another position, said second valve preventing air from leaking from said cuff through said air pump when the air pressure in said cuff is to be maintained constant and allowing air to be vented from said cuff through said air pump when said cuff is to be vented.

5. The blood pressure monitor of claim 4 wherein said second valve allows air to flow between said air pump and said blood pressure cuff when said second valve is de-energized so that said cuff is vented through said air pump in the event of a power loss in said monitor.

6. The blood pressure monitor of claim 5 wherein said bleed valve vents said blood pressure cuff when said bleed valve is de-energized so that said cuff is vented through one of said valves in the event that either of said valves sticks in a position preventing airflow from said blood pressure cuff and said cuff is vented through both of said valves in the event of a power loss in said monitor.

7. The blood pressure monitor of claim 4 wherein said bleed valve vents said blood pressure cuff when said bleed valve is de-energized so that said cuff is vented in the event of a power loss in said monitor.

8. The blood pressure monitor of claim 4, further including a restricting flow leakage vent at said air pump to increase the reverse flow of air through said second valve when said blood pressure cuff is to be vented.

9. A method of operating a blood pressure monitor having an air pump supplying air to a relatively low volume blood pressure cuff, said method preventing air from leaking from said blood pressure cuff through said monitor when the pressure in said cuff is to be maintained at a relatively low value, said method comprising isolating said air pump from said blood pressure cuff when the pressure in said cuff is to be maintained constant, allowing airflow from said air pump to said blood pressure cuff when said cuff is to be inflated and allowing airflow between said air pump and said blood pressure cuff when said blood pressure cuff is to be vented.

* * * * *